United States Patent [19]

Weber et al.

[11] Patent Number: 4,644,067

[45] Date of Patent: Feb. 17, 1987

[54] PROCESS FOR THE EXTRACTION OF AMINO ACIDS FROM AN AQUEOUS PHASE

[75] Inventors: Alfred Weber; Detlef Wilke; Johannes Kurzidim; Mario Kennecke, all of Berlin, Fed. Rep. of Germany

[73] Assignee: Schering Aktiengesellschaft, Berlin and Bergkamen, Fed. Rep. of Germany

[21] Appl. No.: 690,546

[22] Filed: Jan. 11, 1985

Related U.S. Application Data

[63] Continuation of Ser. No. 413,582, Aug. 31, 1982, abandoned.

[30] Foreign Application Priority Data

Aug. 31, 1981 [DE] Fed. Rep. of Germany ....... 3134901

[51] Int. Cl.[4] .................. C07D 209/20; C07C 101/08
[52] U.S. Cl. .................... 548/497; 562/445; 562/433
[58] Field of Search ............. 548/497; 562/516, 445

[56] References Cited

U.S. PATENT DOCUMENTS 2,681,927  7/1954  McCollam et al. ............. 548/497

Primary Examiner—Glennon H. Hollrah
Assistant Examiner—D. B. Springer
Attorney, Agent, or Firm—Millen & White

[57] ABSTRACT

A process for the extraction of aromatic (e.g., phenyl-containing) amino acids from an aqueous phase (solution) containing them, comprising combining the aqueous phase with a tenside of the formula $$R-U-SO_3X$$

wherein
R is alkyl or cycloalkyl each of 4–18 carbon atoms; or phenyl or naphthyl, each optionally substituted by alkyl groups, and having up to 18 carbon atoms total.
U is a carbon-to-sulfur bond or an oxygen atom, and
X is an alkali metal ion;
acidifying the aqueous phase to a pH value of 2.0–2.5; and
extracting the aqueous phase with an alcohol, a ketone, or a carboxylic acid alkyl ester, each containing 4–6 carbon atoms.

15 Claims, No Drawings

PROCESS FOR THE EXTRACTION OF AMINO ACIDS FROM AN AQUEOUS PHASE

This is a continuation of application Ser. No. 413,582 filed Aug. 31, 1982, now abandoned.

BACKGROUND OF THE INVENTION

The present invention concerns a process for extracting aromatic amino acids from an aqueous phase containing them.

In the hydrolysis of proteins and especially also in the fermentative production of amino acids, aqueous phases are obtained in most cases. Dissolved therein are different amino acids. The separation from such mixtures of individual or select groups of amino acids is frequently rather problematic, as is well known.

SUMMARY OF THE INVENTION

It is an object of this invention to provide a process for extracting aromatic amino acids from such aqueous phases in a simple way, while the remaining amino acids (non-aromatic) are extracted only to a small extent under the conditions of this invention.

Upon further study of the specification and appended claims, further objects and advantages of this invention will become apparent to those skilled in the art.

These objects have been attained by providing, per this invention, a process for the extraction of aromatic (e.g. phenyl-containing) amino acids from an aqueous phase (solution) containing them, comprising combining the aqueous phase with a tenside of the formula $$R-U-SO_3X$$

wherein
R is alkyl or cycloalkyl each of 4-18 carbon atoms; or phenyl or naphthyl, each optionally substituted by alkyl groups, and having up to 18 carbon atoms total.
U is a carbon-to-sulfur bond or an oxygen atom, and X is an alkali metal ion; acidifying the aqueous phase to a pH of 2.0-2.5; and extracting the aqueous phase with an alcohol, a ketone, or a carboxylic acid alkyl ester, each containing 4-6 carbon atoms.

DETAILED DISCUSSION

Suitable aqueous phases are, for example, those contained in the fermentative manufacture of L-phenylalanine (see, for example, Chem. Abstr. 76, P 57 722k; 78, P 122 655y; 78, R 146 210a, 82, P 15 274j; and 85, P 121 806f), L-tyrosine (see, for example, Chem. Abstr. 76, P 84 566n; 77, P 60 057y; 78, R 146 210a; 82, P 17 119m; and 85, P 121 806f), 3-hydroxy-L-tyrosine=DOPA (see, for example, Chem. Abstr. 76, P 152 037z; 78, P 157 879b; 80, 144 375a; 81, P 3 699f; and 83, P 7 116q), L-tryptophan (see, for example, Chem. Abstr. 78, P 56, 436z; 78, R 146 220d; 81, P 13 463m; 84, 15 655a); and 5-hydroxy-L-tryptophan (see, for example, Chem. Abstr. 76, P 139 064m; 79, P 103 669; 80, P 13 649v; 80, P 106 876g; and 83, 106 645s), etc. It is basically possible to extract the thus-obtained aqueous micro-organism cultures proper in accordance with this invention. However, in most cases it is more advantageous to filter the same or centrifuge it prior to extraction, and then to process the resultant solutions further in accordance with this invention.

There is nothing particularly critical about the aqueous solution for successful use of this invention. Usually, the aromatic amino acids will be present in the aqueous solutions in concentrations of 0,2-10 wt %, but their concentration is not critical. Other solution components from which the aromatic amino acids are separated in accordance with this invention include normal fermentation media components, non-aromatic or non-phenyl containing amino acids or other such components, as for example proteinhydrolysates.

Examples of suitable tensides of the formula, given above, usable for conducting the process of this invention include: sodium dodecylbenzenesulfonate, sodium pentanesulfonate, sodium hexanesulfonate, sodium heptanesulfonate, sodium octanesulfonate, sodium decanesulfonate, sodium dodecanesulfonate, sodium dodecyl sulfate or sodium heptadecyl sulfate, and commercially available tensides consisting of mixtures of such compounds. An especially preferred tenside is sodium dodecyl sulfate and in general sodium alkyl sulfate of 10-18 C-atoms or sodium alkyl sulfonate of 6-12 C-atoms.

In the above tenside formula, the number of substituents on the phenyl or naphthyl groups is not critical; the important feature is the total number of C-atoms in the R group. A single, long-chain alkyl substituent is preferred.

X is preferably Na but other alkali metals are suitable, e.g., K etc.

The requisite pH is achieved using any compatible acid in sufficient amount to achieve a pH in the described range, such as, sulfuric acid, For conducting the process of this invention, 1.5-5 and especially 2-4 moles of tenside of the general formula is preferably utilized per mole of amino acid to be extracted. The latter can be conventionally estimated, perhaps with a few routine preliminary experiments.

Examples of suitable solvents for conducting the extraction step of this invention include: butyl alcohol, amyl alcohol, sec-amyl alcohol, isoamyl alcohol, hexyl alcohol, methyl butyl ketone, ethyl propyl ketone, methyl isobutyl ketone, methyl pentyl ketone, ethyl acetate, ethyl propionate, ethyl butyrate, propyl acetate, or butyl acetate. Ethyl acetate and methyl isobutyl ketone are especially preferred. As can be seen, the $C_{4-6}$-alcohol, -ketone, or -carboxylic acid ester are all generally aliphatic in nature.

The amount of extractant used depends on the choice of the latter, on the particular amino acid(s) to be extracted, and on the tenside utilized. Suitable ranges are readily determined in each individual case, as is customary, using fully conventional techniques, perhaps with a few routine preliminary experiments.

Typically, the ratio of the amount of extractant to the amount of amino acid to be extracted will fall within the broad range of 30:1 to 500:1 v/v.

The extraction is usually performed at about 15°-40° C. and preferably at room temperature using fully conventional procederes, e.g., with agitation and repetition of extraction.

The aromatic amino acid(s) can be isolated from the extract in a manner known per se, for example by re-extracting the extract with water, binding the amino acid to a strongly acidic ion exchanger, and re-eluting the amino acid with alcoholic ammonia solution. After concentration of the eluate, the amino acid is obtained while the tenside is in the extracted aqueous phase and can be recovered from the latter.

Another possible conventional method, for example, involves binding the tenside to a weakly alkaline ion exchanger and isolating the amino acid from the aqueous phase. It is, of course, also possible to concentrate the extract or the aqueous phase obtained during re-extraction, and isolate the amino acid by crystallization.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In order to obtain meaningful comparable results in these practical examples, a nutrient medium frequently employed for the cultivating of microorganisms was utilized instead of an aqueous microorganism culture.

EXAMPLE 1

100 ml of a nutrient medium containing 5% glucose, 4% corn steep liquor, 2% urea, 0.03% dipotassium hydrogen phosphate, 0.02% potassium dihydrogen phosphate, and 0.01% magnesium chloride (all data refer to gram per liter) is combined with 1.00 g of amino acid and such an amount of sodium dodecyl sulfate that 3 moles of tenside are present per mole of amino acid. The solution is acidified to pH 2.2 and extracted once with 200 ml of ethyl acetate. The content of amino acid in the organic phase is determined by semi-quantitative thin-layer chromatography. The results obtained in this experiment are set forth in the following table.

| Amino Acid Employed | Yield of Extraction |
|---|---|
| Tryptophan | over 90% |
| 5-Hydroxytryptophan | over 90% |
| Phenylalanine | over 90% |
| Tyrosine | about 90% |
| Histidine | 10–20% |
| Serine | 10–20% |
| Lysine | 10–20% |
| Proline | 5–10% |
| Alanine | about 5% |
| Glutamic acid | under 5% |

EXAMPLE 2

500 ml of the nutrient medium disclosed in Example 1 is combined with 2.5 g of tryptophan and 10.0 g of sodium dodecyl sulfate, acidified with sulfuric acid to pH 2.2, and extracted once with 1,000 ml of ethyl acetate. The organic phase is re-extracted with 500 ml of distilled water, the aqueous extract is acidified to pH 2, and filtered over a column of a strongly acidic cation exchanger ("Dowex" 50). The ion exchanger is washed with water and then with 250 ml of 50% 1N alcoholic ammonia solution. The latter is evaporated to dryness under vacuum, yielding a residue containing, per analysis, 91.5% of the tryptophan employed.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for selectively extracting a naturally occurring phenyl-substituted or benz-ring-fused-pyrrolo-containing amino acid or 5-hydroxytryptophan from an aqueous phase containing the same comprising combining the aqueous phase with an alkali metal alkyl sulfate having 10–18 carbon atoms in the alkyl residue;
   acidifying the combination to a pH value of 2.0–2.5; and
   extracting the combination with an extractant which is an aliphatic alcohol, ketone, or carboxylic acid alkyl ester, each containing 4–6 carbon atoms, to produce an extract containing an increased concentration of the naturally occurring phenyl-substituted benz-ring-fused-pyrrolo-containing amino acid or 5-Hydroxytrytophan.

2. A process of claim 1 further comprising separating the amino acid from the resultant extract.

3. A process for the extraction of an amino acid from an aqueous phase of claim 1, wherein the aqueous phase employed is an aqueous microorganism culture of a filtrate or centrifugate thereof.

4. A process for the extraction of an amino acid from an aqueous phase of claim 1, wherein 1.5–5 moles of sulfate is utilized per mole of amino acid to be extracted.

5. A process for the extraction of an amino acid from an aqueous phase of claim 1, wherein the extractant employed is ethyl acetate or methyl isobutyl ketone.

6. A process for the extraction of an amino acid from an aqueous phase of claim 1, wherein the sulfate is sodium dodecyl sulfate or sodium heptadecyl sulfate.

7. A process for the extraction of an amino acid from an aqueous phase of claim 1, wherein the extractant is butyl alcohol, amyl alcohol, sec-amyl alcohol, isoamyl alcohol, hexyl alcohol, methyl butyl ketone, ethyl propyl ketone, methyl isobutyl ketone, methyl pentyl ketone, ethyl acetate, ethyl propionate, ethyl butyrate, propyl acetate, or butyl acetate.

8. A process of claim 1, wherein said extractant is an aliphatic ketone.

9. A process of claim 1, wherein said extractant is an alcohol.

10. A process of claim 1, wherein said extractant is a carboxylic acid alkyl ester.

11. A process of claim 1, wherein the aqueous phase from which the amino acid is extracted is a fermentation medium.

12. A process of claim 1, wherein the extraction is carried out at 15°–40° C. and the ratio of extractant to amino acids is 30:1 to 500:1 v/v.

13. A process of claim 1, wherein the alkali metal is sodium.

14. A process of claim 1, wherein the sulfate is sodium dodecylsulfate.

15. A process for selectively extracting an amino acid from an aqueous phase containing the same comprising combining the aqueous phase with an alkali metal alkyl sulfate having 10–18 carbon atoms in the alkyl residue
   acidifying the combination to a pH value of 2.0–2.5; and
   extracting the combination with an extractant which is an aliphatic alcohol, ketone, or carboxylic acid alkyl ester, each containing 4–6 carbon atoms, to produce an extract containing an increased concentration of L-phenylalanine, L-tryosine, L-3-hydroxytyrosine, L-tryptophan, or L-5-hydroxytryptophan.

* * * * *